United States Patent [19]

Wilson

[11] Patent Number: 5,041,116

[45] Date of Patent: Aug. 20, 1991

[54] COMPRESSION HIP SCREW SYSTEM

[76] Inventor: James T. Wilson, 132 Barrington Dr., Brandon, Fla. 33511

[21] Appl. No.: 525,850

[22] Filed: May 21, 1990

[51] Int. Cl.⁵ ............................................. A61F 5/04
[52] U.S. Cl. ...................................... 606/65; 606/66; 606/69
[58] Field of Search ...................... 606/65, 66, 67, 68, 606/62, 63, 64, 69

[56] References Cited

U.S. PATENT DOCUMENTS

| | | | |
|---|---|---|---|
| 2,612,159 | 9/1952 | Collison | 606/65 |
| 2,702,543 | 2/1955 | Pugh | 606/65 |
| 2,801,631 | 8/1957 | Charnley | 606/65 |
| 3,374,786 | 3/1968 | Callender | 606/65 |
| 3,996,931 | 12/1976 | Callender, Jr. | 606/65 |
| 4,095,591 | 6/1978 | Graham, Jr. | 606/66 |
| 4,438,762 | 3/1984 | Kyle | 606/65 |
| 4,612,920 | 9/1986 | Lower | 606/66 |
| 4,621,629 | 11/1986 | Koeneman | 606/65 |
| 4,628,923 | 12/1986 | Medoff | 606/65 |
| 4,776,329 | 10/1988 | Treharne | 606/65 |
| 4,791,918 | 12/1988 | Von Hasselbach | 606/65 |

FOREIGN PATENT DOCUMENTS

| | | | |
|---|---|---|---|
| 0321170 | 6/1989 | European Pat. Off. | 606/65 |
| 2209947 | 6/1989 | United Kingdom | 606/65 |

Primary Examiner—Danton D. DeMille
Assistant Examiner—Michael Brown
Attorney, Agent, or Firm—Dominik, Stein

[57] ABSTRACT

An improved compression hip screw system including a lag screw having a first end with external threads insertable into the proximal end of a femur head and broken fragments thereof and having a second end with an axial bore; a barrel/side plate having a plate-like member attachable at its distal end to a femur and having a barrel at its proximal end for receiving the second end of the lag screw; a compression screw within the barrel and extending into the bore of the lag screw, a supplemental set screw threaded through the barrel/side plate to secure the compression screw in a fixed position with respect to the barrel/side plate; and a coupling device joining the lag screw and compression screw to allow a telescoping motion between the lag screw and the compression screw in the event of axial movement of the broken fragment and lag screw with respect to the proximal end of the femur and the barrel/side plate.

7 Claims, 1 Drawing Sheet

COMPRESSION HIP SCREW SYSTEM

BACKGROUND OF THE INVENTION

1. Field of the Invention

This invention relates to a compression hip screw system and, more particularly, to an improved self-compressing hip lag screw with mechanisms to retain the compression screw fixed with respect to the barrel/side plate and with the lag screw and compression screw coupled so as to preclude lateral movement of the compression screw into the hip muscle while still allowing normal bone impaction and lag screw collapse/movement laterally.

2. Description of the Background Art

The hip joint is the most heavily stressed load carrying bone joint of the human body. It is essentially a ball and socket joint formed by the top of the femur which pivots within the up-shaped acetabulum at the base of the pelvis. When a break or fracture occurs adjacent to the top of the femur, the separated portions of the femur must be held together while healing occurs.

Various mechanisms for holding bone portions together during healing are in commercial use today while others are disclosed in the patient literature. The most common devices are compression hip screws of one design or another. Such devices may utilize as lag screw extended through an aperture bored through the upper part of the femur and its broken fragment to hold the fragment in proper position with respect to the majority of the femur during healing. A side plate is screwed to the femur. The side plate has a barrel at its upper end for receiving the lag screw. A compression screw secures the lag screw to the side plate. Devices of this nature are disclosed in U.S. Pat. No. 2,397,545 to Harding; 4,621,629 to Koeneman; 4,628,923 to Medoff; 4,432,358 to Fixel; and 4,438,762 to Kyle.

All of the known prior art, whether in the patent literature as disclosed above, or in commercial devices, fails to take into account the shifting of the lag screw and its compression screw in the barrel as the break heals and the fragments move closer together. When this movement occurs, the head of the compression screw moves laterally away from the break and into the soft tissue causing discomfort, pain and a painful bursa.

As illustrated by the background art, efforts are continuously being made in an attempt to improve compression hip screw systems. No prior effort, however, provides the benefits attendant with the present invention. Additionally, the prior patents and commercial techniques do not suggest the present inventive combination of component elements arranged and configured as disclosed and claimed herein.

The present invention achieves its intended purposes, objects, and advantages through a new, useful and unobvious combination of component elements, with the use of a minimum number of functioning parts, at a reasonable cost to manufacture, and by employing only readily available materials.

Therefore, it is an object of this invention to provide an improved compression hip screw system comprising a lag screw having a first end with external threads insertable into the proximal end of a femur head and broken fragments thereof and having a second end with an axial bore; a barrel/side plate having a plate-like member attachable at its distal end to a femur and having a barrel at its proximal end for receiving the second end of the lag screw; a compression screw within the barrel and extending into the bore of the lag screw; a supplemental set screw threaded through the barrel/side plate to secure the compression screw in a fixed position with respect to the barrel/side plate; and coupling means joining the lag screw and compression screw to allow a telescoping motion between the lag screw and the compression screw in the event of axial movement of the broken fragment and lag screw with respect to the proximal end of the femur and the barrel/side plate.

It is a further object of the present invention to preclude movement of a compression screw away from a bone being healed.

It is a further object of this invention to take up the movement of a intertrocanteric fracture during healing through the intercoupling of a lag screw and a barrel/side plate.

The foregoing has outlined some of the more pertinent objects of this invention. These objects should be construed to be merely illustrative of some of the more prominent features and applications of the present invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with the specific embodiment shown in the attached drawings. For the purpose of summarizing the invention, the invention may be incorporated into an improved compression hip screw system comprising a lag screw having a first end with external threads insertable into the proximal end of a femur head and broken fragments thereof and having a second end with an axial bore; a barrel/side plate having a plate-like member attachable at its distal end to a femur and having a barrel at its proximal end for receiving the second end of the lag screw; a compression screw within the barrel and extending into the bore of the lag screw; a supplemental set screw threaded through the barrel/side plate to secure the compression screw in a fixed position with respect to the barrel/side plate; and coupling means joining the lag screw and compression screw to allow a telescoping motion between the lag screw and the compression screw in the event of axial movement of the broken fragment and lag screw with respect to the proximal end of the femur and the barrel/side plate.

The coupling means includes a fixed end wall secured to the distal end of the bore through which the compression screw may freely move to mate with a movable washer within the bore coupled by threads to the compression screw. The fixed end wall has an aperture in axial alignment with a threaded aperture of the washer functioning as an alignment guide for the alignment of the compression screw with respect to the washer. The compression hip screw system further includes an abutment collar located within the barrel through which the compression screw is positioned with the head of the compression screw in contact therewith. The distal end wall and washer are in contact with each other upon initial implantation of the system. The washer moves away from the distal end wall during healing of the break and movement of the bore fragments toward each other.

In addition, the invention may also be incorporated into an improved compression hip screw system comprising a lag screw having a first end with external threads insertable into the proximal end of a femur head and broken fragments thereof and having a second end with an axial bore; a barrel/side plate having a plate-like member attachable at its distal end to a femur and having a barrel at its proximal end for receiving the second end of the lag screw; a compression screw within the barrel and extending into the bore of the lag screw; a supplemental set screw threaded through the barrel/side plate to secure the compression screw in a fixed position with respect to the barrel/side plate; and coupling means including a fixed distal end wall secured to the exterior end of the bore through which the compression screw may freely move and align to mate with a movable washer within the bore threadedly coupled to the compression screw and joining the lag screw and compression screw to allow a telescoping motion between the lag screw and the compression screw in the event of axial movement of the broken fragment and lag screw with respect to the upper end of the femur and the barrel/side plate.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the disclosed specific embodiment may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF THE DRAWINGS

For a fuller understanding of the nature and objects of the present invention, reference should be made to the following detailed description taken in conjunction with the accompanying drawings in which.

Similar reference characters refer to similar parts throughout the several Figures.

DETAILED DESCRIPTION OF THE INVENTION

Figure 1:
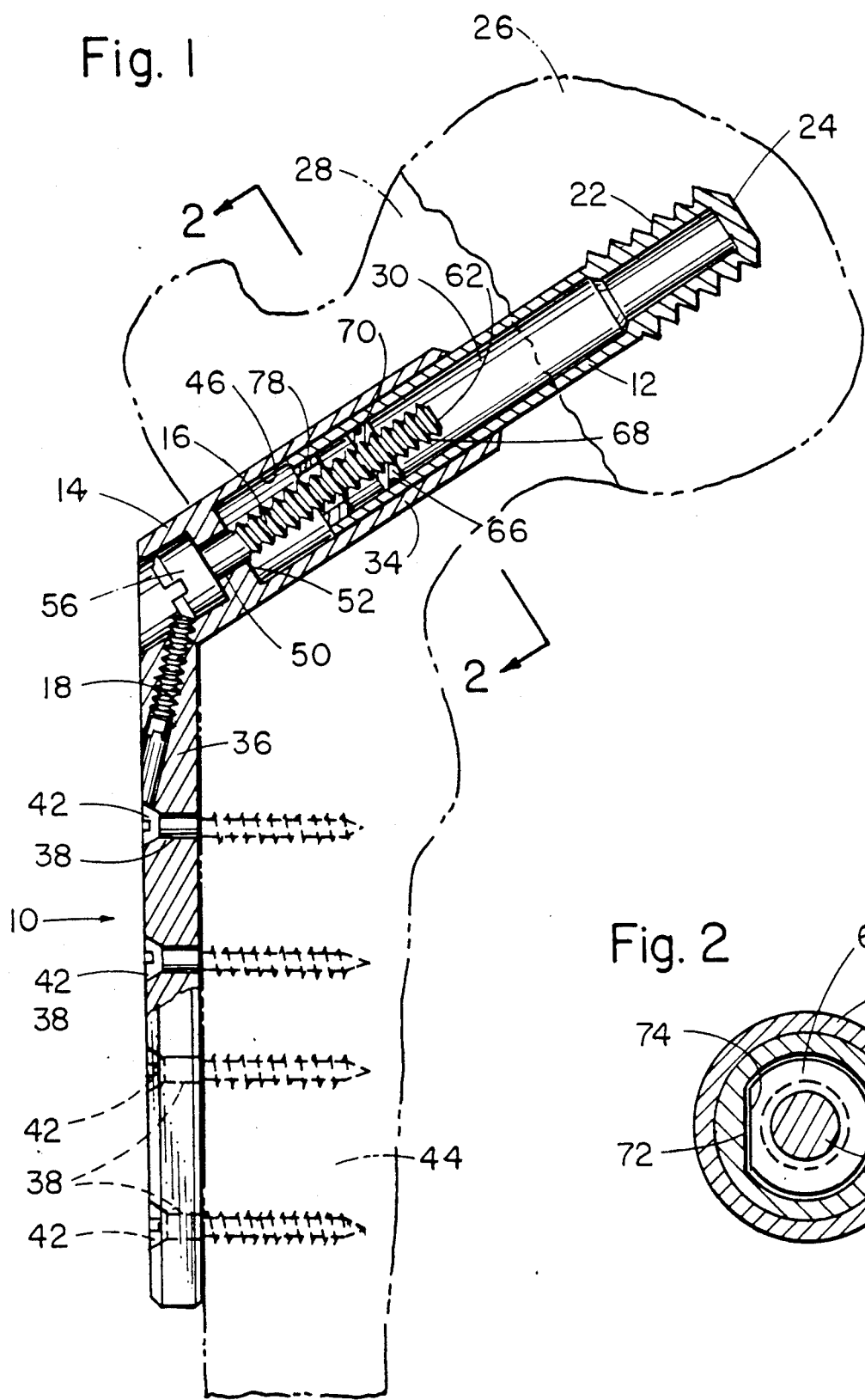
FIG. 1 is a sectional view of a compression hip screw constructed in accordance with the principles of the present invention shown in association with a broken proximal femur.
Figure 2:
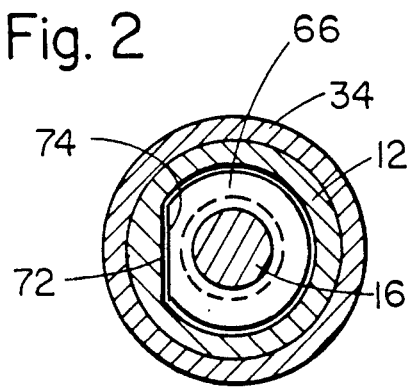
FIG. 2 is a sectional view of the compression hip screw shown in FIG. 1 taken along line 2—2 of FIG. 1 thereof.

Shown in FIG. 1 is a two-part system 10 consisting of a lag screw 12 and barrel/side plate member 14. Also included as part of the system 10 are an associated compression screw 16 and a set screw 18.

The lag screw 12 is formed with external threads 22 at its proximal end 24 adapted to be screwed into one part 26 of a broken femur head 28. The distal part of the lag screw 12 is provided with an axial bore 30 for coaxially receiving the compression screw 16 in a manner to be described hereinafter.

The barrel/side plate 14 is integrally fabricated to include a barrel 34 and a side plate 36. Formed of lower portion of the barrel/side plate 14 is the side plate 36. The side plate has aligned apertures 38 adapted to receive screws 42 for coupling to the femur 44. On the upper portion of the barrel/side plate 14 is the barrel 34. The barrel has a central aperture 46 for receiving the distal end of the lag screw 12. A compression screw 16 extends through an aperture 50 in an abutment collar 52 formed in the barrel 34. The compression screw 16 is then threaded into the lower end of the lag screw 12 so that upon screwing the compression screw 16 into the lag screw 12, with the head 56 of the compression screw 16 in contact with the abutment collar 52, the bone parts will be in mating contact with each other to promote healing.

Unfortunately, during use, the lag screw often moves down and laterally away from the broken bone fragment, as shown in FIG. 1, so that the head of the compression screw impinges in soft tissue of the patient thereby causing discomfort and a painful bursa.

A recent improvement in commercial use today employs an additional set screw. Such additional set screw is to be located through the barrel to make contact with the compression screw. This precludes the compression screw from moving down and laterally into the pain-creating orientation. Such device, however, does not allow for the natural shifting of the set screw with respect to the lag screw as is needed for proper bone healing.

The present invention relates to accommodating any movement of the compression screw 16 and set screw 18 by taking up any lag screw 12 movement within the distal end of the lag screw 12 and the proximal end 62 of the compression screw 16. More specifically, the lower distal end of the lag screw 12 is formed with a bore 30. The washer 66 is located in the bore 30 of the lag screw 12 and is provided with internal threads for receiving the external threads 68 of the compression screw 16. This washer 66 is slidable within the bore 30 of the lag screw 12 and has a flat side 72 in contact with a flat surface 74 within the bore 30 so as to preclude rotation of the washer 66 with respect to the lag screw 12.

Formed on the external periphery of washer 66 is an annular recess. Located within the annular recess is an O-ring 70 with its exterior most surface positioned outside of the recess in contact with the interior cylindrical surface of lag screw 12. The washer 66 is thus allowed to move within the lag screw with the O-ring in sliding frictional contact therewith. This relationship allows the person installing the lag screw to insert the compression screw into the lag screw and into threaded engagement with washer 66 without having undue sliding movement of the washer as might be caused by the compression screw.

A distal end wall or flange 78 of the lag screw 12 is also provided. Its exterior surface is welded or otherwise. fixedly secured to the inner surface of the bore 30 of the lag screw 12 at the end of the bore. A central, unthreaded hole allows the compression screw to move therethrough. The unthreaded hole in the end wall 78, in effect, acts as an alignment guide for the compression screw as it couples with the threads of the washer and also functions as a seal for the end of the lag screw 12. In this manner, the compression screw 16 may thread into the inner threaded washer 66 for effectively coupling the lag screw 12 and the compression screw 16.

Movement between the lag screw 12 and compression screw 16 is allowed due this arrangement of parts. More specifically, the end wall 78 closes the end of the lag screw bore 30 and thereby provides for initial compression between the lag screw 12 and compression screw 16. The length of the bore 30 limits the degree of compression and the movement between the lag screw 12 and the compression screw 16. Other factors limiting the degree of movement between the lag screw 12 and compression screw 16 are the distance between the distal end of the lag screw 12 and the abutment collar 52, the length of the lag screw 12 versus the abutment collar 52, the amount of bone compressing achieved initially, etc.

When the bone is healing, a natural and beneficial force of the body is generated tending to move the lag screw 12 and the compressing screw 16 laterally and downwardly as seen in FIG. 1. Such force exhibits itself by the lag screw 12 telescoping with respect to the threaded washer 66 and compressing screw 16. This precludes the compressing screw 16 from moving to a pain-causing orientation and permits the bone fragments to be further compressed upon weight bearing. In other words, when initially implanted, the compression screw 16 is screwed in to the lag screw 12 until the washer 66 and the distal end wall 78 of the lag screw 12 are in contact with each other. Upon the later application of force of the lag screw 12 during bone healing and movement, the lag screw 12 will move along its axis with respect to the compression screw 16. The position of the compression screw 16 is fixed. This preferred movement occurs instead of moving the head 56 of the compressing screw 16 into a harmful location. The lag screw 12 and its distal wall 78 simply slide with respect to the compression screw 16. Pain caused by the compression screw 16 protruding into the lateral hip muscle of the patient is thus avoided.

The present disclosure includes that contained in the appended claims as well as that of the foregoing description. Although this invention has been described in its preferred forms with a certain degree of particularity, it is understood that the present disclosure of the preferred forms has been made only by way of example and numerous changes in the details of construction and combination and arrangement of parts may be resorted to without departing from the spirit and scope of the invention.

Now that the invention has been described,

What is claimed is:

1. An improved compression hip screw system comprising:
    a lag screw having a first end with external threads insertable into the proximal end of a femur head and broken fragments thereof and having a second end with an axial bore,
    a barrel/side plate having a plate-like member attachable at its distal end to a femur and having a barrel at its proximal end for receiving the second end of the lag screw;
    a compression screw within the barrel and extending into the bore of the lag screw;
    a supplemental set screw threaded through the barrel/side plate and into an axial bore of said barrel in order to secure the compression screw in a fixed position with respect to the barrel/side plate and;
    coupling means joining the lag screw and compression screw to allow a sliding telescoping motion of the lag screw with respect to the compression screw and the barrel in the event of axial movement of the broken fragment and lag screw with respect to the proximal end of the femur and the barrel/side plate.

2. The compression hip screw system as set forth in claim 1 wherein the coupling means includes a fixed end wall secured to the distal end of the bore through which the compression screw may freely move to mate with a movable washer within the bore coupled by threads to the compression screw.

3. The compression hip screw system as set forth in claim 2 wherein in the fixed end wall has an aperture in axial alignment with a threaded aperture of the washer functioning as an alignment guide for the alignment of the compression screw with respect to the washer.

4. The compression hip screw system as set forth in claim 2 wherein the washer moves away from the distal end wall during healing of the break and movement of the bone fragments toward each other.

5. The compression hip screw system as set forth in claim 1 and further including an abutment collar located within the barrel through which the compression screw is positioned with the head of the compression screw in contact therewith.

6. The compression hip screw system as set forth in claim 1 wherein the distal end wall and washer are in contact with each other upon initial implantation of the system.

7. An improved compression hip screw system comprising:
    a lag screw having a first end with external threads insertable into the proximal end of a femur head and broken fragments thereof and having a second end with an axial bore,
    a barrel/side plate having a plate-like member attachable at its distal end to a femur and having a barrel at its proximal end for receiving the second end of the lag screw;
    a compression screw within the barrel and extending into the bore of the lag screw;
    a supplemental set screw threaded through the barrel/side plate and into an axial bore of said barrel in order to secure the compression screw in a fixed position with respect to the barrel/side plate and;
    coupling means including a fixed distal end wall secured to the exterior end of the bore through which the compression screw may freely move and align to mate with a movable washer slidable within the bore and threadedly coupled to the compression screw and joining the lag screw and compression screw to allow a sliding telescoping motion of the lag screw with respect to the compression screw and the barrel in the event of axial movement of the broken fragment and lag screw with respect to the upper end of the femur and the barrel/side plate.

* * * * *